United States Patent [19]

Kirsch et al.

[11] Patent Number: 4,929,240
[45] Date of Patent: May 29, 1990

[54] SURGICAL CLIP AND APPLIER

[75] Inventors: Wolff M. Kirsch; Zhu Y. Hua, both of Albuquerque; Robert B. Cushman, Cedar Crest, all of N. Mex.

[73] Assignee: University of New Mexico, Albuquerque, N. Mex.

[21] Appl. No.: 135,445

[22] Filed: Dec. 21, 1987

Related U.S. Application Data

[60] Division of Ser. No. 787,101, Oct. 15, 1985, Pat. No. 4,733,660, and a continuation-in-part of Ser. No. 556,917, Dec. 1, 1983, Pat. No. 4,586,503.

[51] Int. Cl.$^5$ .............................................. A61B 17/12
[52] U.S. Cl. .................................... 606/151; 606/142; 606/155
[58] Field of Search ........... 128/335, 346, 325, 334 C, 128/337; 72/410; 606/142, 151, 155

[56] References Cited

U.S. PATENT DOCUMENTS

| 3,098,232 | 7/1963 | Brown | 72/410 |
| 3,110,899 | 11/1963 | Warren | 128/335 |
| 3,150,379 | 9/1964 | Brown | 128/335 |
| 3,203,220 | 8/1965 | Kaepernik | 128/335 |
| 3,616,497 | 11/1971 | Esposito, Jr. | 128/346 |
| 3,827,438 | 8/1974 | Kees, Jr. | 128/346 |
| 4,590,937 | 5/1986 | Daniega | 128/346 |

FOREIGN PATENT DOCUMENTS

| 460112 | of 1913 | France | 128/335 |
| 2150440A | 7/1985 | United Kingdom | 606/151 |

Primary Examiner—Randall L. Green
Assistant Examiner—Gary Jackson
Attorney, Agent, or Firm—Charles Fallow; Martin Hoffman

[57] ABSTRACT

A surgical clip is disclosed having a pair of spaced arms joined by a bridge that is deformed by pulling on a tang, which is connected to the bridge by a frangible neck. Also disclosed is a tool for pulling the tang, and an anastomosis procedure that may be quickly performed using the clip and tool.

5 Claims, 5 Drawing Sheets

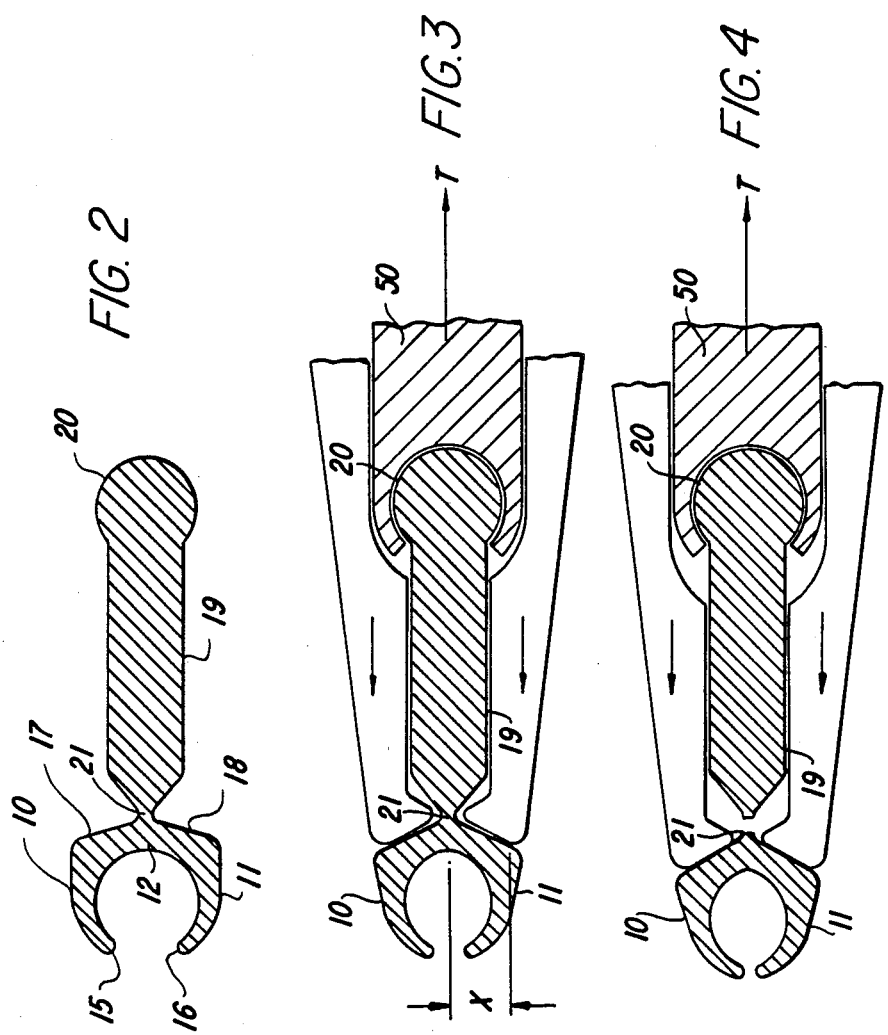

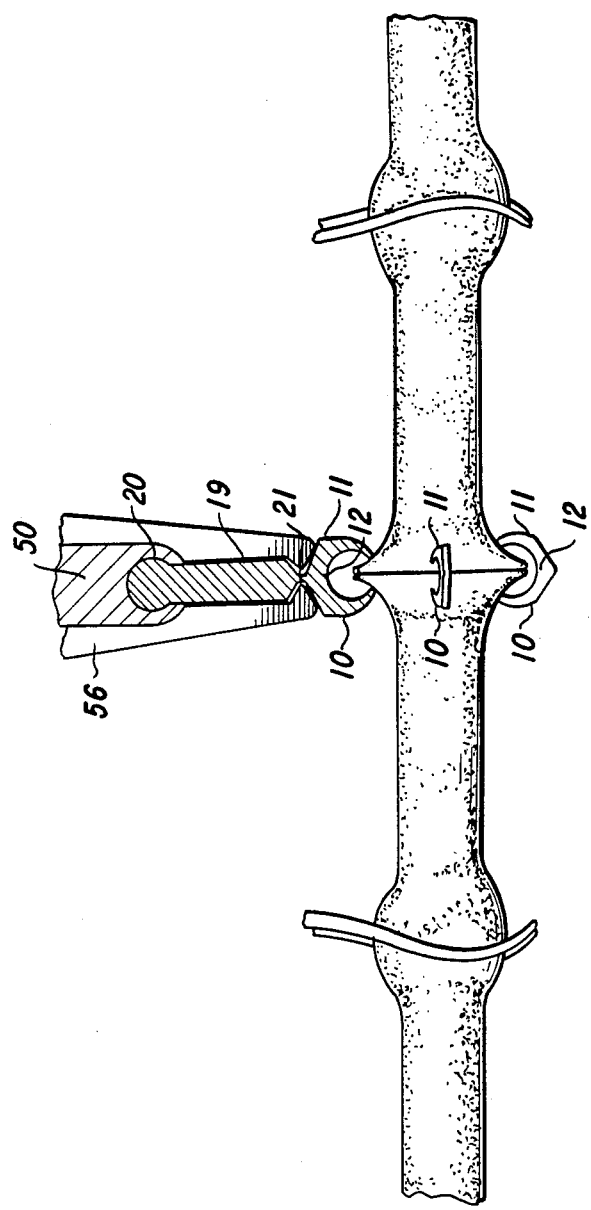

SURGICAL CLIP AND APPLIER

This application is a division of application Ser. No. 787,101, filed Oct. 15, 1985, now U.S. Pat. No. 4,733,660, which has a continuation-in-part of application Ser. No. 556,917, filed Dec. 1, 1983, now U.S. Pat. No. 4,586,503.

BACKGROUND OF THE INVENTION

This invention relates generally to the field of surgery, and more particularly to the field of vascular microsurgery.

In various surgical procedures, it is necessary to unite or reunite very small blood vessels, nerves and the like. The procedure of joining blood vessels is known as vascular anastomosis. Particularly in neurosurgical procedures and in the reattachment of severed body members, the number of anastomoses required can be very numerous, and accordingly, it is advantageous and frequently necessary to perform each such connection quickly yet properly.

A conventional end-to-end anastomosis is illustrated in FIG. 1, which shows a pair of vessels 1 and 2, each held by a respective clamp 3 or 4 while it is sutured around its circumference. The vessel ends are first approximated by inward traction on the two vascular clamps. The vessels may then be preliminarily interconnected by placing sutures at two, three or four spaced locations around the circumference of the vessel—note the threads 5 and 6 in tension—whereafter the suturing 7 is completed with a needle 8. Various suturing techniques are known, all of which are designed to: (a) provide a leak-proof connection; (b) provide adequate tensile strength; (c) avoid unnecessary restriction of the vessel; (d) avoid unnecessary tearing and other trauma to the vessel; and (e) promote rapid and thorough healing. Some of these objectives become increasingly difficult to satisfy as smaller and smaller anastomoses are carried out; furthermore, the danger of accidentally catching the rear or distal wall of a vessel with the needle as the proximal wall is being sutured increases with diminishing vessel sizes.

With all vascular suturing techniques, thrombosis or clotting tends to occur at the points of needle penetration. While this clotting would not usually be sufficient to occlude larger vessels, in smaller veins and arteries a significant constriction or complete occlusion of the vessel can result from clotting. The problem has been summarized thus: "It is apparent to us that the damage to vascular endothelium caused by the microvascular needle perforation is considerable. The amount of subsequent platelet aggregation and clot formation can be extensive, and these platelets are known to release vasoactive substances that can alter vessel diameter. This could diminish blood flow through a 1- to 2-mm vascular anastomosis expected to give immediate increased flow to an underperfused region of the brain." D. Pagnanelli et al, *The Cutting Edge Microsurgical Needle*, Journal of Neurosurgery, volume 59, no. 3, pages 510–512 (Sept. 1983).

In addition to the physiological damage done by suturing, it is also significant that suturing, particularly of small vessels, is a very tedious time-consuming procedure which can preoccupy and fatigue a surgeon over the course of a long procedure. A more rapid way of performing microvascular anastomoses could free the surgeon for other tasks, and could shorten surgical procedures as well. The need for a workable, rapid, non-suturing technique for microsurgery is obvious.

Various non-suture devices and techniques for performing anastomoses are known, particularly for intestinal and colorectal anastomoses, for which various stapling apparatus and methods have been known for some years. Known stapling techniques, however, require penetration of the organ wall, and if applied to vascular anastomoses, the problems of clotting and the like, as described above, could be expected to arise. For vascular anastomosis, various other non-suture mechanical clamps have been suggested. Such clamps frequently include a permanent or sacrificial ferrule or the like and means for clamping the vessel against the ferrule so that penetration of the vessel wall is avoided. However, clamps of this type have not gained widespread acceptance.

In view of the foregoing, this invention has been made with a view to substantially increasing the speed of microvascular anastomoses and other procedures while avoiding the clotting problems caused by conventional suturing procedures. Another object is to reduce the material costs and duration of microsurgical procedures.

A further object of the invention is to provide a permanently implantable surgical clip for use in place of microvascular suturing. Yet another object is to provide the surgeon with a clip that can be easily held and applied during vascular anastomoses.

This invention relates generally to a surgical procedure such as an anastomosis wherein a pair of tissues is approximated, then partially everted, and then joined by placing the arms of a surgical clip over the adjoined tissues and crimping the arms about the tissues in such a way as to hold the tissues together without penetrating them.

The invention is also directed to a vascular surgical clip comprising a plastically deformable body portion, a tang for deforming the body, and a neck connecting the tang to the body, wherein the neck is designed to break upon application of a predetermined tensile force to the tang, and the body being designed to deform upon application to the tang of less than said predetermined tensile force.

In a further aspect, the invention is directed to a tool for applying the subject clip. In its broadest sense, the tool includes means for gripping and applying tension to the tang, and means for simultaneously pushing against shoulders on the clip body. The tool enables the surgeon to perform the subject method by using the tool first to manipulate the clip into position over opposed tissues. Then, by squeezing or otherwise manipulating the tool, he deforms the clip so as to capture the tissues between the clip's arms and thereby hold the tissues permanently together.

BRIEF DESCRIPTION OF THE DRAWINGS

The invention is illustrated by the following description of a preferred embodiment and by the drawings, wherein:

FIG. 2 is an oblique view of the inventive clip in its original, undeformed condition;

FIG. 3 is a view similar to FIG. 2 showing the clip in a partially deformed condition;

FIG. 4 shows the clip in its fully deformed condition;

FIG. 7 is a view similar to FIG. 1, illustrating the inventive procedure.

DESCRIPTION OF THE PREFERRED EMBODIMENT

Figure 1:
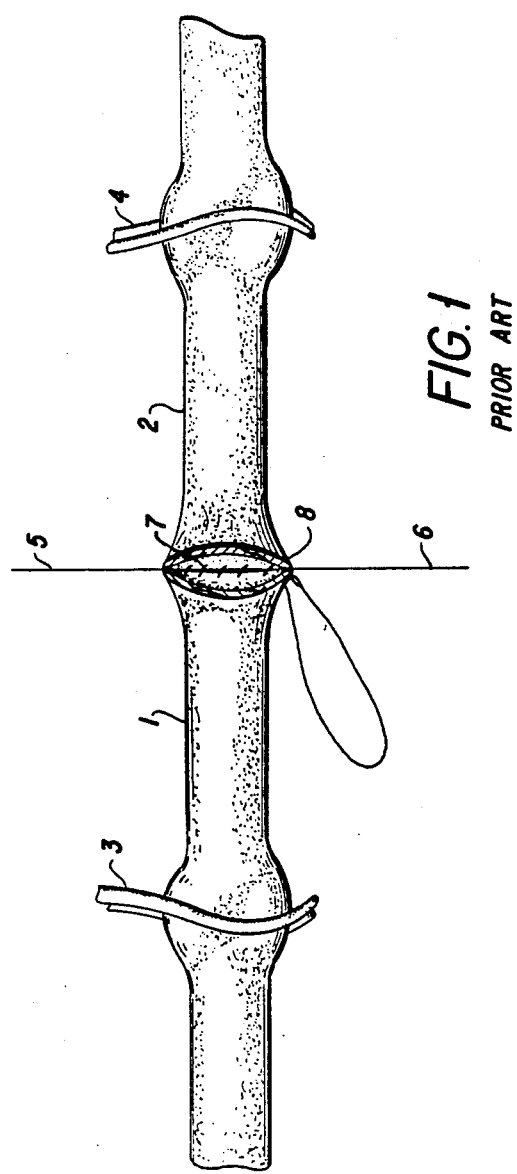
FIG. 1 illustrates a prior art suturing method described above.

As shown in FIG. 2, a surgical clip embodying the invention is formed of a unitary piece of biologically acceptable, plastically deformable material such as a noble metal (i.e. gold, silver, platinum, etc.). While metal clips are presently preferred, it is contemplated that other materials such as suitable polymer plastics may be used. Whatever the material, it must be sufficiently ductile or plastically deformable so that when the clip is crimped there is minimal spring-back. Otherwise, possibly injurious overcrimping, to compensate for the spring-back, would be required.

Structurally, the clip includes a pair of inwardly curved arms 10 and 11 interconnected by a bridging section 12, the two arms extending generally parallel in one direction from the bridging section. The arms terminate at tips 15 and 16 which are rounded to prevent injury to the subject tissue in accordance with an object of this invention. The bridge portion 12 includes a pair of shoulders 17, 18 for engaging the applier tool described below. The center of the bridge is integrally connected to a tang 19 preferably having an enlarged head 20. The connection point is a neck 21 of reduced cross-section designed to break when a predetermined tension is applied to the tang by the tool. The size of the necks is such that its breaking strength ("predetermined tensile force" in the claims below) is greater than the tension required to deform, by bending, the bridge portion of the clip.

The size of the clip will naturally vary according to the application, and we do not intend to limit the scope of this invention to any particular size clip. However, merely as an example, for the anastomiosis of a 1-mm vessel, an appropriate size clip has an overall height on the order of 0.030 inches and an overall thickness on the order of 0.006 inches. For this size clip, the radius of curvature of the tip of each arm is approximately 0.0005 inches.

The deform the clip, tension is applied to the tang 19 by a tool such as that described below, while the shoulders are supported by stationary jaw faces on the tool (FIG. 2). The relationship of the jaw faces and the clip shoulders is preferably such that the points of engagement are substantially spaced; i.e., such points are initially remote from the neck. Because of this geometry, application of a tension T to the tang produces a bending moment M=TX/2 at the center of the bridge, where X equals the distance from the tang axis to either contact point, as shown in FIG. 3. The neck is sufficiently strong that a bending moment large enough to deform the bridge portion can be produced (FIG. 3). In designing the applier and the clip, the abutting surfaces of the clip shoulders and the jaw faces are so designed that once a desired degree of bending deformation has occurred, the contact points move much closer to the neck, whereafter even substantially increased tang tension does not generate a bending moment sufficient to cause bridge deformation, but rather ultimately fractures the neck 21 (FIG. 4). A particular advantage of this feature is that the amount of bridge deformation is acccurately determined by the clip/tool geometry, and is thus independent of the surgeon's manipulating force. As a result, the deformation from clip to clip and from surgeon to surgeon is highly reproducible for a given clip/tool combination. Furthermore, one of skill in the art will appreciate how simple changes in jaw face geometry or clip shoulder shape could be made to produce desired changes in the degree of clip deformation.

Figure 5:
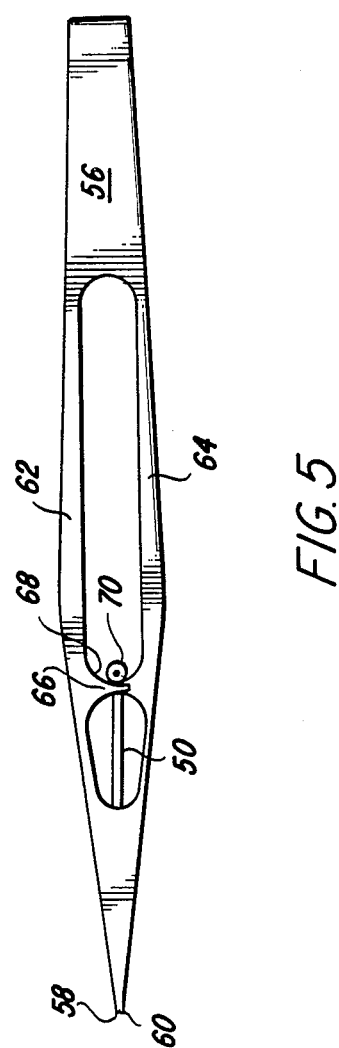
FIG. 5 is an elevational view of the inventive clip applier.
Figure 6:
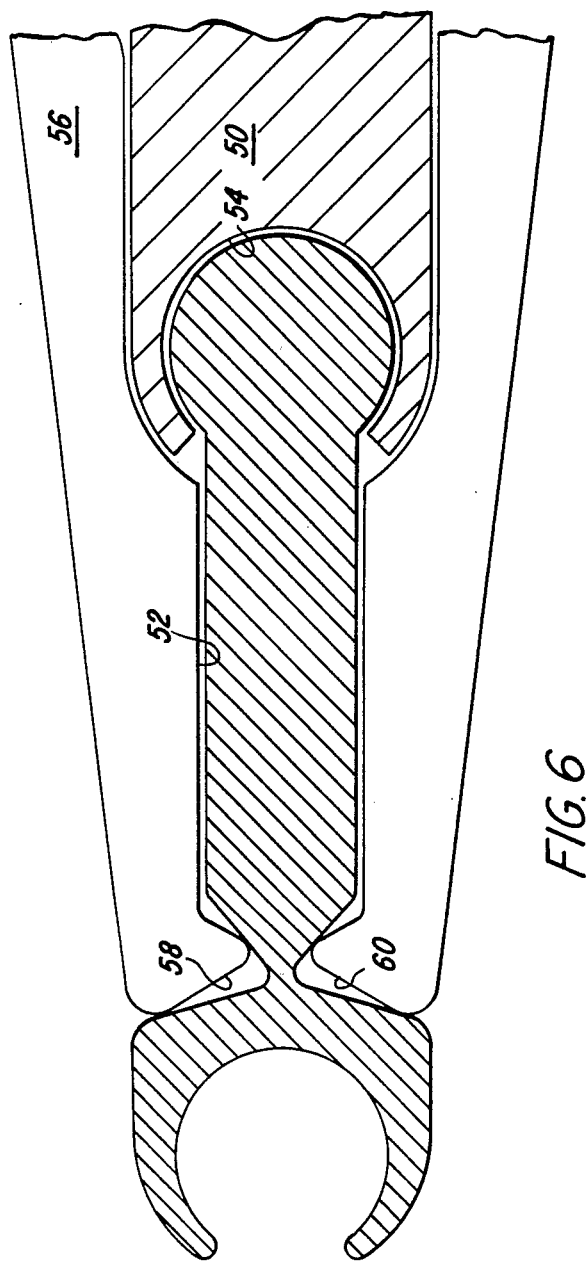
FIG. 6 is an enlarged view of a portion of FIG. 5.

FIGS. 5 and 6 show a clip applier constructed in accordance with this invention. The applier includes means for gripping a clip tang, preferably in the form of a single movable jaw 50 having a slot 52 sized to receive the tang, which slot has an enlarged pocket or recess 54 sized to receive the tang's head. The jaw is supported in a body 56 that terminates at a forward end defined by stationary jaw faces 58, 60 astride the slot and designed to engage the shoulders 17, 18 on the clip. In the embodiment shown, the jaw faces 58, 60 are planar and have between them an obtuse angle of approximately 120°, which is less than the angle B of approximately 150° between the clip shoulders. Comparing FIGS. 3 and 4, one will note the inward shift in contact point location which results from this geometry as the clip deforms.

The jaw is retracted away from the abutment faces by any of several mechanisms, most preferably a cam-actuated device responsive to squeezing pressure from the surgeon's hand. In this embodiment, shown in FIG. 5, the applier body 56 includes a pair of flexible leaves 62,64 interconnected at both ends and movable toward each other when the tool is squeezed by the surgeon. Each leaf has an inner surface from which a cam 66 protrudes, the cam having an actuating surface 68 oblique to its direction of movement. As viewed in FIG. 5, the cams are symmetrical in profile, and overlap so as jointly to engage a common cam follower 70. This follower is connected to the jaw 50 as shown. When the leaves are squeezed together, the cam surfaces approach one another, causing the movable jaw 50 to retract with respect to the stationary jaw faces 58,60. When a clip is in place within the tool, this action causes deformation as previously described. In FIG. 5 the arcuate shape of the cam faces 68 is noteworthy. This shape makes the ratio of squeezing force to retracting force an increasing function, giving better feel in situations where it is desired intentionally to limit clip deformation to less than that dictated by the shapes of the abutting surfaces.

While the retracting mechanism is preferably purely mechanical for reasons of simplicity, other mechanisms, such as a fluid-driven piston, or an electrically actuated solenoid, are also contemplated. In any event, what is required is a safe, reliable mechanism for retracting the jaw with respect to the body, responsive to a simple manipulation by the surgeon.

It will be appreciated that the proper geometry for the clip depends on the shape of the applier's jaw and abutment surfaces, and vice-versa. Therefore, these two items must be cooperatively designed.

FIG. 7 illustrates an end-to-end microvascular anastomosis employing the clip and applier described above. In this procedure, a pair of tissues to be joined are first drawn together in apposition (approximated) by suitable means. The edges of the tissues should be partially everted, that is, pursed or flanged outwardly approximately 90° from the axial direction, so that a clip can be placed over the tissue edges, with the arms of the clip astride the point of apposition. Care must be taken not to allow the vessel to cuff back over on itself, since the joint ultimately produced would be weaker than the flanged configuration. Once the clip has been positioned properly with respect to the subject tissues, crimping is effected simply by squeezing together the leaves of the tool. This causes permanent deformation of the microclip bridge section 12, whereafter the clip arms 10,11 retain the tissues in apposition without puncturing them. This procedure is repeated at as many points as are needed to join the subject tissues securely. The clips, being biologically inert, ordinarily may be left in place permanently. However, in the event that the clip must be removed, a suitable tool may be used to spread the arms 10 and 11.

The clip and applier tool described above provide a sutureless means for the apposition of tissue which is substantially faster than conventional suturing methods, particularly in microvascular anastomosis and which avoids the clotting problem caused by needle perforations. In testing on femoral arteries in rats, short and long term patency and remarkably little damage to the vascular endothelium have been observed.

An advantage of the inventive clips over sutures is the predictability of results. In contrast to hand-made micro-suturing needles, the mass-produced microclips are uniform, producing more uniform results.

An additional advantage is that the speed of application reduces the time blood supply is interrupted, enhancing prospects for vessel patency.

Another advantage is that on any tissues joined in accordance with this invention, the clips are physically independent of one another. Thus, although they securely hold the tissues together at individual points, the clips can move with respect to one another. As a result, their spacing can increase as tissues grow. This makes the present invention particularly attractive for performing anastomoses in children, whose vessels must later expand. Permanent sutures (FIG. 1) must of course be removed if they are not to interfere with vessel growth.

It should be understood that the foregoing description and drawing described and illustrate but one embodiment of the invention, whose scope should be measured by the following claims.

We claim:

1. A surgical clip for permanently joining apposed tissues, comprising
    a bridge portion made of a plastically deformable material,
    a pair of spaced arcuate arms extending generally parallel in one direction from opposite ends of said bridge, each of said arms having a concave surface facing the other arm, and said arms terminating at distal tips which are sufficiently rounded to avoid puncturing tissue captured therebetween,
    a tang extending from said bridge in a direction opposite that of said arms,
    a neck connecting said tang to said bridge,
    said neck being breakable upon application of a predetermined tensile force to said tang,
    a pair of spaced shoulders on said bridge portion, one on either side of said neck, for supporting said clip as tension is applied to said tang, to create a bending moment in said bridge for deforming the same,
    said bridge being of such dimensions as to be plastically and permanently deformed by bending upon application to the tang of a force less than said predetermined tensile force while the clip is supported by a tool engaging its shoulders, said bending closing said arms around said apposed tissues, said plastically and permanently deformed bridge retaining said arms in their closed positions after said tang is broken away.

2. The invention of claim 1, further comprising an enlarged head on said tang to facilitate gripping thereof by an applier tool.

3. The invention of claim 1, wherein said shoulders have generally flat surfaces for limiting deformation of said bridge when tension is applied to said tang.

4. The invention of claim 3, wherein said shoulders lie at an obtuse angle in the range of 120° to 180° with respect to one another.

5. The invention of claim 3, wherein said shoulders lie at an obtuse angle of about 120° with respect to one another.

* * * * *